(12) United States Patent
Starner et al.

(10) Patent No.: US 6,759,503 B2
(45) Date of Patent: Jul. 6, 2004

(54) CURING EPOXY RESIN WITH N-CYANOETHYLATED TOLUENEDIAMINES

(75) Inventors: William Edward Starner, Nesquehoning, PA (US); Tammy Lynn Cush, Whitehall, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/355,547

(22) Filed: Jan. 31, 2003

(65) Prior Publication Data

US 2003/0144540 A1 Jul. 31, 2003

Related U.S. Application Data

(62) Division of application No. 10/024,976, filed on Dec. 19, 2001, now Pat. No. 6,593,487.

(51) Int. Cl.⁷ .................. C07C 255/03; C08G 59/50
(52) U.S. Cl. .................. 528/123; 525/523; 558/394
(58) Field of Search .................. 528/123, 523; 558/394

(56) References Cited

U.S. PATENT DOCUMENTS 4,196,145 A * 4/1980 Halasz et al. .................. 260/573

FOREIGN PATENT DOCUMENTS

| EP | 0067593 | 5/1982 |
|----|---------|--------|
| JP | 2963739 | 8/1999 |

OTHER PUBLICATIONS

"Handbook of Epoxy Resins" by H. Lee and K. Neville, McGraw Hill Book Co. 1967.

Ashcroft, W.R., "Curing Agents for Epoxy Resins," in B. Ellis (ed.).

"Chemistry and Technology of Epoxy Resins," Blackie Academic and Professional, London (1993).

Elderfield, et al., 68 J. Amer. Chem. Soc. 1262 (1949).

Cookson, et al., "The Cyanoethylation of Amines and Arsines," J. Chem. Soc. 1949.

Braunholtz, et al., "The Preparation of Bis(2–cyanoethyl) Derivatives of Aromatic Primary Amines, and Their Conversion into 1:6–Diketojulolidines," J. Chem. Soc., 1952.

Braunholtz, et al., "The Preparation of Bis(2–cyanoethyl) Derivatives of Aromatic Primary Amines, and Their Conversion into 1:6–Diketojulolidines, Part II," J. Chem. Soc., 1953.

* cited by examiner

Primary Examiner—Robert Sellers
(74) Attorney, Agent, or Firm—Michael Leach

(57) ABSTRACT

The invention provides N-cyanoethylated toluenediamines (CNTDAs), processes for synthesizing them, and compositions containing them. In preferred embodiments, the CNTDAs are represented by the following formula:

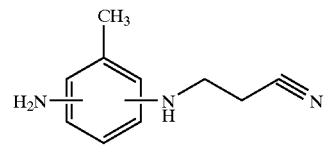

where the nitrogen atoms are ortho or meta to each other on the aromatic ring. The CNTDAs are particularly suitable for use as latent curing agents for epoxy resins.

9 Claims, No Drawings

CURING EPOXY RESIN WITH N-CYANOETHYLATED TOLUENEDIAMINES

This application is a division of application Ser. No. 10/024,976 filed Dec. 19, 2001, now U.S. Pat. No. 6,593,487.

BACKGROUND OF THE INVENTION

This invention relates to aromatic amines, more particularly to N-cyanoethylated ortho-toluenediamine and N-cyanoethylated meta-toluenediamine, a process for making them, and their use as epoxy curing agents.

It is known to use amines, such as aliphatic or aromatic amines, for the curing of epoxy resins. See, e.g., "Handbook of Epoxy Resins" by H. Lee and K. Neville, McGraw Hill Book Co., 1967. The aromatic amines currently available provide high Tg, good fracture toughness and excellent chemical resistance for adhesive and composite applications, but suffer from several shortfalls. Aromatic amines typically used as epoxy curatives, such as methylenedianiline (MDA) and diethyltoluenediamine (DETDA), are usually considered to be highly toxic. In addition, the potlife of such aromatic amines is of an insufficient duration to consider the amines to be latent curatives. MDA and DETDA, for example, have very long potlives of up to 12 to 24 hours, but do not provide a potlife of several days, which is desired in a latent curing agent. Moreover, such aromatic amines cannot be used with solid epoxy resins for powder coating applications.

The epoxy industry has employed many types of curative blends in an attempt to maximize the desired application properties, but in most cases at the expense of other properties. Additives such as accelerators, tougheners, reactive diluents and non-reactive diluents are employed to maximize a desired property but again to the deterioration of other properties. A number of good references are available on this subject including: Lee and Neville's, "Handbook of Epoxy Resins," cited above, and W. R. Ashcroft, "Curing Agents for Epoxy Resins," in B. Ellis (ed.). "Chemistry and Technology of Epoxy Resins," Blackie Academic and Professional, London (1993), pp. 37–73.

Others in the epoxy industry have developed novel amines in attempting to optimize curative properties. For example, Japanese Patent 2963739 (1999) describes the use of substituted-N-phenyl-1,3-propanediamines as liquid epoxy curatives which do not B-stage during cure and thus yield a fully cured epoxy resin. The substituted-N-phenyl-1,3-propanediamines described therein are represented by the following chemical formula:

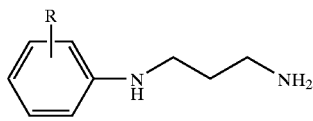

where R is hydrogen, lower alkyl group, lower alkoxyl group or halogen. Although the method of synthesis of these curatives is not disclosed, other references teach methods for synthesizing aromatic amines.

For example, European Patent 0 067 593 (1982) describes the cyanoethylation of para, meta, and ortho phenylenediamine to generate 3,3'-(p,m or o-phenylenedi-imino)-dipropanenitrile:

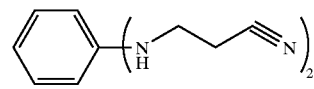

EP 0 067 593 teaches the use of water as the solvent and concentrated hydrochloric acid as the catalyst to obtain the dicyanoethylated product.

Elderfield et al., 68 J. Amer. Chem. Soc. 1262 (1949), describes the synthesis of β-p-anisidinopropionitrile by boiling p-anisidine and acrylonitrile in acetic acid.

Cookson et al., "The Cyanoethylation of Amines and Arsines," J. Chem. Soc. 1949, pp. 67–72, describes the cyanoethylation of aniline by heating to 150° C. a mixture of aniline and acrylonitrile in the presence of excess acetic acid in an autoclave to generate 2-cyanoethylaniline and bis-2-cyanoethylaniline. The reference further describes the reaction of diphenylamine and acrylonitrile in an excess of acetic acid using a catalytic amount of fine copper powder to generate diphenyl-2-cyanoethylamine.

Braunholtz et al., "The Preparation of Bis(2-cyanoethyl) Derivatives of Aromatic Primary Amines, and Their Conversion into 1:6-Diketojulolidines," J. Chem. Soc., 1952, pp. 3046–3051, describes the cyanoethylation of aniline, m-toluidine, p-toluidine, p-anisidine and p-chloroaniline in an excess of acetic acid.

Braunholtz et al., "The Preparation of Bis(2-cyanoethyl) Derivatives of Aromatic Primary Amines, and Their Conversion into 1:6-Diketojulolidines. Part II," J. Chem. Soc., 1953, pp. 1817–1824, describes the cyanoethylation of several different aromatic primary monoamines in an excess of acetic acid using various metal catalysts to selectively generate mono and di-cyanoethylated derivatives.

All references cited herein are incorporated herein by reference in their entireties.

BRIEF SUMMARY OF THE INVENTION

The invention provides cyanoethylated toluenediamines, processes for synthesizing them, compositions containing them and methods for using them to cure epoxy resins. In preferred embodiments, the cyanoethylated toluenediamines are represented by the following formula:

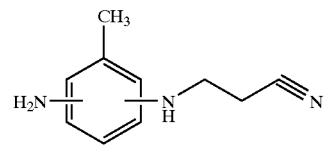

where the nitrogen atoms are ortho or meta to each other on the aromatic ring.

With regard to the present invention and throughout the specification and claims the terms "cyanoethyl toluenediamine(s)", "cyanoethylated toluenediamine(s)", "N-(cyanoethyl) toluenediamine(s)" and "N-(cyanoethylated) toluenediamine(s)" are used interchangeably.

DETAILED DESCRIPTION OF THE INVENTION

The most preferred cyanoethylated toluenediamines of the invention are suitable for use as epoxy resin curing agents. Cyanoethylated toluenediamines where the nitrogen atoms are ortho or meta to each other on the aromatic ring have been found to be particularly suitable for this purpose.

Thus, the most preferred cyanoethylated toluenediamines of the invention are cyanoethylated products of ortho-toluenediamine represented by the following Formulas I–IV:

(I)
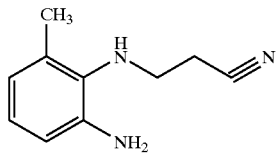
N-(2-amino-6-methylphenyl)-3-aminopropionitrile (II)
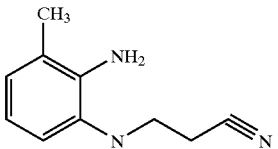
N-(2-amino-3-methylphenyl)-3-aminopropionitrile (III)
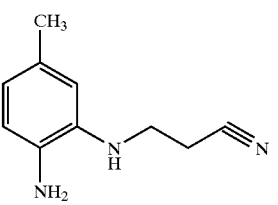
N-(2-amino-5-methylphenyl)-3-aminopropionitrile (IV)
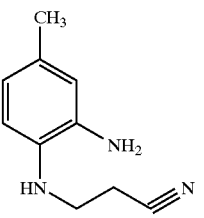
N-(2-amino-4-methylphenyl)-3-aminopropionitrile and cyanoethylated products of meta-toluenediamine represented by the following Formulas V–VII:

(V)
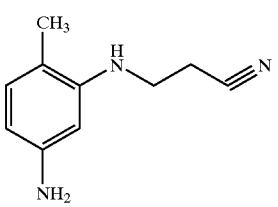
N-(3-amino-6-methylphenyl)-3-aminopropionitrile (VI)
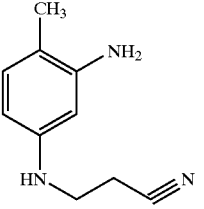
N-(3-amino-4-methylphenyl)-3-aminopropionitrile (VII)
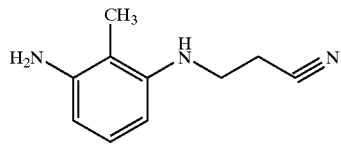
N-(5-amino-6-methylphenyl)-3-aminopropionitrile Formulas I–IV above are the cyanoethylated products of ortho-toluenediamine (OTD). Formulas I–II are based on 2,3-toluenediamine (TDA) and Formulas III–IV are based on 3,4-TDA. A commercial isomer mix of OTD is typically 60/40 2,3-TDA/3,4-TDA. Using commercial grade OTD therefore leads to cyanoethylated isomer mixtures.

Formulas V–VII above are the cyanoethylated products of meta-toluenediamine (MTD). Formula V is based on 2,6-TDA and Formulas VI and VII are based on 2,4-TDA.

Cyanoethylated products of OTD are prepared by reacting OTD with acrylonitrile (ACN) at elevated temperature in the presence of an acid and a protic solvent (e.g., water) for a period of time adequate for reaching the desired extent of conversion to the cyanoethylated product. Cyanoethylated products of MTD are prepared by reacting MTD with ACN at elevated temperature in the presence of an acid and a protic solvent (e.g., water) for a period of time adequate for reaching the desired extent of conversion to the cyanoethylated product. The following equation illustrates a preferred cyanoethylation reaction of the invention.

Cyanoethylation

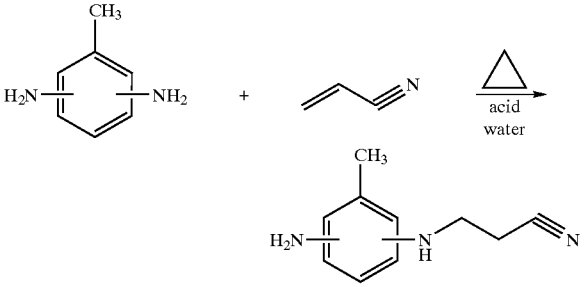

In the preparation of cyanoethylated OTD, either the pure compounds 2,3-TDA or 3,4-TDA, or isomer mixtures, such as 60/40 2,3-TDA/3,4-TDA, can be reacted with ACN. In fact, any blend or mixture of the TDA isomers may be used. The preferred reactant mixture comprises commercial grade OTD.

In the preparation of cyanoethylated MTD, either the pure compounds 2,4-TDA, 2,6-TDA, or isomer mixtures such as 80/20 2,4-TDA/2,6-TDA can be reacted with ACN. Any blend or mixture of the TDA isomers can be used. The preferred reactant mixture comprises commercial grade MTD.

The molar ratio of reactants, moles of OTD and/or MTD to moles of ACN, can vary from about 10:1 to about 1:10. The molar ratio used will affect the rate of reaction and the product distribution, but as the final product is purified, the final product quality is unaffected. To maximize yield and efficiency, the desired molar ratio is from 0.95:1.0 to about 1.0:2.0 with the optimum being about 1.0:1.2.

The cyanoethylation reaction is conducted using at least one acid catalyst. The acid catalyst can be any mineral, carboxylic, super or supported acid, including but not limited to hydrochloric acid, sulfuric acid, phosphoric acid, acetic acid, propionic acid, para-toluenesulfonic acid, triflic acid (trifluoromethanesulfonic acid) and Nafion® super acid catalyst from DuPont, which is a bead-form strongly acidic resin, i.e., a copolymer of tetrafluoroethylene and perfluoro-3,6-dioxa-4-methyl-7-octenesulfonyl fluoride, converted to the proton (H+) form. The preferred acid catalysts are hydrochloric acid and Nafion catalyst with Nafion catalyst being most preferred.

Any protic solvent can be used in the cyanoethylation, including but not limited to water, methanol, ethanol, isopropanol, n-propanol, etc.

The cyanoethylation reaction can be conducted over a temperature range from about 50° C. to about 150° C. within a pressure range of from about atmospheric pressure up to about 900 psi (6.21 MPa). The reaction time is dependent on the reaction temperature, pressure and the desired extent of the reaction as measured by gas chromatography (GC). The reaction of TDA with ACN can generate not only a mono-cyanoethylated product (CNTDA) but also a di-cyanoethylated product (DCNTDA). Thus, at any given time during the cyanoethylation there is, for example, a mixture of unreacted TDA, CNTDA and DCNTDA, as described according to the following Equation V:

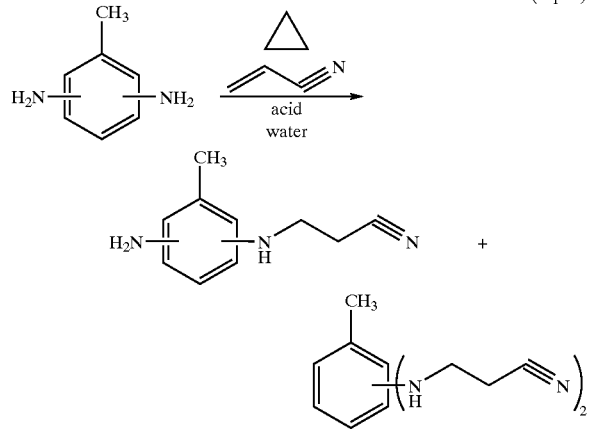

(Eq. V)

The cyanoethylated product mixture can be hydrogenated to provide aminopropylated TDAs, which are also useful as epoxy curing agents. Such aminopropylated TDAs and a process for making them, are disclosed in the inventors' copending U.S. application Ser. No. 10/024,974 also filed Dec. 19, 2001 U.S. Pat. No. 6,441,238.

Purification

The crude product resulting from cyanoethylation is a slurry mixture of starting TDA, the desired mono-cyanoethylated TDA (in the case of OTD, cyanoethylated OTD or CNOTD, and in the case of MTD, cyanoethylated MTD or CNMTD), di-cyanoethylated TDA byproduct (DCNOTD and/or DCNMTD), water and catalyst. The composition of the organic portion of the crude slurry product will vary depending on the reaction conditions, catalyst type and reaction time. Typical composition ranges for OTD-based reactions are 20/70/10 to 5/75/20 weight % OTD/CNOTD/DCNOTD. Typical composition ranges for MTD-based reactions are 20/70/10 to 5/75/20 weight % OTD/CNMTD/DCNMTD. Although the crude product is satisfactory as a curative for epoxy resins, it is more desirable to use the purified CNOTD and/or CNMTD. This purification may be accomplished by any method known to one skilled in the art, but the preferable method is simply washing the crude cyanoethylated TDA with a solvent, such as methanol, ethanol, propanol or isopropanol, again a method well known to the art. Very high purity cyanoethylated TDA can be obtained by recrystallization of the crude cyanoethylated TDA in an appropriate solvent, such as those listed above for washing the crude cyanoethylated TDA (although the washing and recrystallization solvents need not be identical). Depending on the washing or recrystallization conditions, the purified product can have an assay ranging from about 90 to 99.9% with the chief impurities being TDA and di-cyanoethylated TDA byproduct, with a small amount of acid catalyst. Again, none of these impurities will impair the performance attributes imparted by this curative to a cured epoxy resin formulation.

Use of Cyanoethylated Aromatic Amines as Epoxy Curatives

The crude, purified and high purity grades of cyanoethylated toluenediamine are mixed thoroughly with an epoxy resin and heated to effect curing. The stoichiometry employed preferably ranges from 0.5 N—H equivalent of the CNTDA per equivalent of epoxide moieties in the epoxy resin to 1.5 N—H equivalent of the CNTDA per equivalent of epoxide. More preferably, the stoichiometry ranges from 0.9 to 1.1 N—H equivalent per epoxide with a 1.0:1.0 ratio being most preferred.

Any epoxy resin can be employed, including but not limited to the diglycidyl ether of bisphenol A and/or bisphenol F. Solvents such as an alcohol, phenol, aliphatic or aromatic hydrocarbon, esters, ethers and the like can be used. Reactive diluents such as aromatic and aliphatic glycidyl ethers and esters can also be used as well as various types of fillers and colorants.

The cyanoethylated aromatic amines of the invention are excellent curatives for epoxy resins, providing both latency and the performance properties of an aromatic amine curative, particularly chemical resistance and Tg. In addition, the amines of the invention are solids at room temperature.

The invention will be illustrated in more detail with reference to the following Examples, but it should be understood that the present invention is not deemed to be limited thereto.

EXAMPLE 1

Cyanoethylation of 3,4-Toluenediamine Using Nafion Catalyst

A 3000 ml 4-necked round bottom flask was equipped with a mechanical stirrer, thermometer, condenser, nitrogen purge and dropping funnel. The vessel was charged with 500 parts of 3,4-toluenediamine, 436 parts of deionized water and 3.0 parts of Nafion catalyst. The mixture was heated to 80–86° C. and 322 parts of ACN were added drop-wise over a thirty-minute period. The mixture was refluxed for 11 hours, cooled to room temperature and collected. The organic phase of the reaction mixture contained 3.2% acrylonitrile, 5.4% 3,4-toluenediamine, 80.1% mono-cyanoethylated 3,4-toluenediamine (CN-3,4-OTD) and 11.2% di-cyanoethylated 3,4-toluenediamine (DCN-3,4-OTD), according to gas chromatography (GC) analysis. The crude CN-3,4-OTD reaction mixture was filtered to collect the CN-3,4-OTD product, washed with ethanol and dried in air. An 80% yield of CNOTD (573 g) was obtained, which had a melting point of 124.8° C. The CNOTD as analyzed by GC contained 0.2% OTD, 99.1% CNOTD and 0.7% DCNOTD.

Use of Purified CN-3,4-OTD as Epoxy Curative

The purified CN-3,4-OTD was mixed with Epon 828 epoxy resin and evaluated for heat of reaction and Tg by Differential Scanning Calorimetry (DSC). Thus, 33.0 g of CN-3,4-OTD were added to 100.0 g of Epon 828 and mixed thoroughly for 2 minutes using high shear agitation. The DSC data obtained immediately after mixing were: Onset Temperature of 99° C., Maximum Heat of 145° C., ΔH of 325 j/g and Tg of 114° C.

The purified CN-3,4-OTD was mixed with DER 642 solid powdered epoxy resin and evaluated for heat of reaction and Tg by DSC. Thus, 2.92 g of CN-3,4-OTD were added to 26.5 g of DER 642U and mixed thoroughly for 30 minutes using a ball mill. The DSC data obtained immediately after mixing were: Onset Temperature of 96° C.; Maximum Heat of 145° C.; ΔH of 190 j/g and Tg of 146° C.

EXAMPLE 2

Cyanoethylation of 60/40 2,3-/3,4-OTD Using Hydrochloric Acid as Catalyst

A 2000 ml 4-necked round bottom flask was equipped with a mechanical stirrer, thermometer, condenser, nitrogen purge and dropping funnel. The vessel was charged with 523 parts of OTD, 502 parts of deionized water and 0.3 parts of concentrated hydrochloric acid. The mixture was heated to 80–86° C. and 477 parts of ACN were added drop-wise over a 30-minute period. The mixture was refluxed for 28 hours, cooled to room temperature and collected. The organic phase of the reaction mixture contained 15.4% ACN, 10.4% OTD, 59.8% mono-cyanoethylated 2,3-/3,4-toluenediamine (CNOTD) and 13.6% di-cyanoethylated 2,3-/3,4-toluenediamine (DCNOTD), according to GC analysis.

EXAMPLE 3

Cyanoethylation of 60/40 2,3-/3,4-OTD Using Nafion Catalyst

A 2000 ml 4-necked round bottom flask was equipped with a mechanical stirrer, thermometer, condenser, nitrogen purge and dropping funnel. The vessel was charged with 523.5 parts of OTD, 505 parts of deionized water and 1.0 parts of Nafion catalyst. The mixture was heated to 80–86° C. and 477 parts of ACN were added drop-wise over a 30-minute period. The mixture was refluxed for 23 hours, cooled to room temperature and collected. The organic phase of the reaction mixture contained 8.8% ACN, 19.5% OTD, 61.1% CNOTD and 9.8% DCNOTD according to GC analysis. The crude CNOTD reaction mixture was filtered to collect the CNOTD product, washed with ethanol and dried in air. A 54% yield of CNOTD (405 g) was obtained, which had a melting point of 111.7° C. The CNOTD as analyzed by GC contained 0.35% OTD, 99.65% CNOTD and 0.0% DCNOTD.

Use of Purified CNOTD as Epoxy Curative

The purified CNOTD was mixed with Epon 828 epoxy resin and evaluated for heat of reaction and Tg by DSC. Thus, 33.0 g of CNOTD were added to 100.0 g of Epon 828 and mixed thoroughly for 2 minutes using high shear agitation. The DSC data obtained immediately after mixing were: Onset Temperature of 85.4° C., Maximum Heat of 147° C., ΔH of 302 j/g and Tg of 144° C.

EXAMPLE 4

Cyanoethylation of 3,4-toluenediamine Using 1-Propanol as Solvent

A 500 ml 4-necked round bottom flask was equipped with a magnetic stir bar and stirrer, thermometer, condenser, nitrogen purge and dropping funnel. The vessel was charged with 104.8 parts of 3,4-toluenediamine, 100 parts of 1-propanol and 0.3 parts of Nafion catalyst. The mixture was heated to 80–86° C. and 95 parts of acrylonitrile were added drop-wise over a 30-minute period. The mixture was refluxed for 46 hours, cooled to room temperature and collected. The organic phase of the reaction mixture contained 10.3% acrylonitrile, 25.6% 3,4-toluenediamine, 50.9% mono-cyanoethylated 3,4-toluenediamine and 7.2% di-cyanoethylated 3,4-toluenediamine according to GC analysis.

EXAMPLE 5

Cyanoethylation of 2,4-toluenediamine Using Nafion Catalyst

A 5000 ml 4-necked round bottom flask was equipped with a mechanical stirrer, thermometer, condenser, nitrogen purge and dropping funnel. The vessel was charged with 54.7 parts (0.45 mole) of 2,4-toluenediamine, 49.0 parts of deionized water and 0.3 parts of Nafion catalyst. The mixture was heated to 76° C. and 47.3 parts (0.9 mole) of ACN were added drop-wise over a 30-minute period. The mixture was refluxed for 16 hours, cooled to room temperature and collected. The organic phase of the reaction mixture contained 10.7% acrylonitrile, 1.7% 2,4-toluenediamine, 71.3% mono-cyanoethylated 2,4-toluenediamine (CN-2,4-MTD) and 14.9% di-cyanoethylated 2,4-toluenediamine (DCN-2,4-MTD), according to GC analysis. The crude CN-2,4-MTD reaction mixture was phase separated to remove the aqueous layer and dried under reduced pressure at 125° C. A 96% yield of CN-2,4-MTD (76 g) was obtained which was a dark viscous liquid. The crude CN-2,4-MTD had an amine value of 312.2 meg KOH/g.

Use of Crude CN-2,4-MTD as Epoxy Curative

The crude CN-2,4-MTD was mixed with Epon 828 epoxy resin and evaluated for heat of reaction and Tg by DSC. Thus, 3.3 g of CN-2,4-MTD were added to 10.0 g of Epon 828 and mixed thoroughly for 2 minutes using high shear agitation. The DSC data obtained immediately after mixing were: Onset Temperature of 140° C., Maximum Heat of 187° C., ΔH of 374 j/g and Tg of 116° C.

EXAMPLE 6

Cyanoethylation of 80/20 2,4-/2,6-Toluenediamine Using Nafion Catalyst

A 500 ml 4-necked round bottom flask was equipped with a mechanical stirrer, thermometer, condenser, nitrogen purge and dropping funnel. The vessel was charged with 55.15 parts (0.45 mole) of 80/20 2,4-/2,6-toluenediamine, 54.6 parts of deionized water and 0.26 parts of Nafion catalyst. The mixture was heated to 86° C. and 47.7 parts (0.9 mole) of ACN were added drop-wise over a 30-minute period. The mixture was refluxed for 24 hours, cooled to room temperature, phase separated, dried at 125° C. under reduced pressure and collected. The crude cyanoethylated 2,4-/2,6-toluenediamine reaction mixture was a dark viscous liquid containing 3.2% 2,4-/2,6-toluenediamine, 70.8% monocyanoethylated 2,4-/2,6-toluenediamine and 24.4% dicyanoethylated 2,4-/2,6-toluenediamine according to GC analysis.

Use of Crude CN-2,4-/2,6-toluenediamine as Epoxy Curative

The crude cyanoethylated 2,4-/2,6-toluenediamine was mixed with Epon 828 epoxy resin and evaluated for heat of reaction and Tg by DSC. Thus, 3.3 g of cyanoethylated 2,4-/2,6-toluenediamine were added to 10.0 g of Epon 828 and mixed thoroughly for 2 minutes using high shear agitation. The DSC data obtained immediately after mixing were: Onset Temperature of 148° C., Maximum Heat of 194° C., ΔH of 372 j/g and Tg of 127° C.

EXAMPLE 7

Cyanoethylation of 80/20 2,4-/2,6-Toluenediamine Using Nafion Catalyst

A 3000 ml 4-necked round bottom flask was equipped with a mechanical stirrer, thermometer, condenser, nitrogen purge and dropping funnel. The vessel was charged with 1033 parts (8.5 mole) of 80/20 2,4-/2,6-toluenediamine, 1047 parts of deionized water and 1.0 parts of Nafion catalyst. The mixture was heated to 80–86° C. and 669 parts (12.6 mole) of ACN were added drop-wise over a 30-minute period. The mixture was refluxed for 23 hours, cooled to room temperature, phase separated and collected. The crude cyanoethylated reaction mixture contained 2.1% 2,4-/2,6-toluenediamine, 71.9% cyanoethylated 2,4-/2,6-toluenediamine and 5.6% di-cyanoethylated 2,4-/2,6-toluenediamine according to GC analysis.

Purification of Cyanoethylated 2,4-/2,6-toluenediamine

The crude cyanoethylated 2,4-/2,6-toluenediamine was washed twice with 500 mL of water, dissolved in 1 liter of 1-propanol and filtered to remove Nafion catalyst. The filtrate was transferred to a 3-liter round bottom flask equipped with a magnetic stirrer, thermocouple, nitrogen bubbler, 18-inch packed column with condenser, vacuum connecter and collection flask. The vessel contents were slowly heated to 125° C., during which time the 1-propanol was distilled off. Once at 125° C., the pressure of the system was slowly reduced to 10 mm Hg. A heart cut was taken over a distillation temperature range of 180–190° C. at 10 mm Hg. The heart cut obtained was found to contain 0.4% 2,4-/2,6-toluenediamine, 98.2% monocyanoethylated 2,4-/2,6-toluenediamine and 1.4% dicyanoethylated 2,4-/2,6-toluenediamine. The semisolid purified cyanoethylated 2,4-/2,6-toluenediamine had a melting range of 33–60° C. The purified cyanoethylated 2,4-/2,6-toluenediamine was then recrystallized 2 times from isopropanol to obtain a purple crystalline solid with a melting point of 63° C. and a GC analysis of 0.0% 2,4-/2,6-toluenediamine, 98.9% cyanoethylated 2,4-/2,6-toluenediamine and 1.1% dicyanoethylated 2,4-/2,6-toluenediamine.

Use of Purified CN-2,4-/2,6-toluenediamine as Epoxy Curative

The purified cyanoethylated 2,4-/2,6-toluenediamine was mixed with Epon 828 epoxy resin and evaluated for heat of reaction and Tg by DSC. Thus, 3.3 g of cyanoethylated 2,4-/2,6-toluenediamine were added to 10.0 g of Epon 828 and mixed thoroughly for 2 minutes using high shear agitation. The DSC data obtained immediately after mixing were: Onset Temperature of 146° C., Maximum Heat of 186° C., ΔH of 379 j/g and Tg of 112° C.

While the invention has been described in detail and with reference to specific examples thereof, it will be apparent to one skilled in the art that various changes and modifications can be made therein without departing from the spirit and scope thereof.

What is claimed is:

1. In a method of curing an epoxy resin with a curing composition containing an amine, the improvement wherein the amine is a di-cyanoethylated toluenediamine or a mono-cyanoethylated toluenediamine other than N-(3-amino-6-methylphenyl)-3-aminopropionitrile, wherein the di-cyanoethylated toluenediamine or mono-cyanoethylated toluenediamine is mixed with an epoxy resin and reacted to effect curing.

2. The method of claim 1, wherein said mono-cyanoethylated toluenediamine is represented by the following formula:

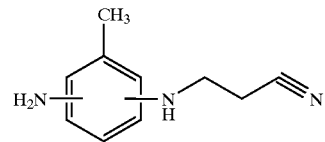

where the nitrogen atoms are ortho or meta to each other on the aromatic ring.

3. The method of claim 1, wherein said mono-cyanoethylated toluenediamine is N-(2-amino-6-methylphenyl)-3-aminopropionitrile.

4. The method of claim 1, wherein said mono-cyanoethylated toluenediamine is N-(2-amino-3-methylphenyl)-3-aminopropionitrile.

5. The method of claim 1, wherein said mono-cyanoethylated toluenediamine is N-(2-amino-5-methylphenyl)-3-aminopropionitrile.

6. The method of claim 1, wherein said mono-cyanoethylated toluenediamine is N-(2-amino-4-methylphenyl)-3-aminopropionitrile.

7. The method of claim 1, wherein said mono-cyanoethylated toluenediamine is N-(5-amino-6-methylphenyl)-3-aminopropionitrile.

8. The method of claim 1, wherein said mono-cyanoethylated toluenediamine is N-(3-amino-6-methylphenyl)-3-aminopropionitrile.

9. The method of claim 1, wherein said mono-cyanoethylated toluenediamine is N-(3-amino-4-methylphenyl)-3-aminopropionitrile.

* * * * *